United States Patent
Perouse

[11] Patent Number: 6,110,147
[45] Date of Patent: Aug. 29, 2000

[54] SELF-PROTECTED INJECTION SYRINGE

[75] Inventor: Eric Perouse, L'Isle Adam, France

[73] Assignee: Societe d'Etudes d'Applications Techniques-Sedat, Irigny, France

[21] Appl. No.: 08/981,660
[22] PCT Filed: Jul. 8, 1996
[86] PCT No.: PCT/FR96/01066
 § 371 Date: Jan. 8, 1998
 § 102(e) Date: Jan. 8, 1998
[87] PCT Pub. No.: WO97/02855
 PCT Pub. Date: Jan. 30, 1997

[30] Foreign Application Priority Data

Jul. 12, 1995 [FR] France .................. 95 08462

[51] Int. Cl.⁷ .............................. A61M 5/32
[52] U.S. Cl. .......................... 604/198; 604/110
[58] Field of Search .................. 604/192, 196, 604/198, 200, 221, 228, 229, 86, 412, 413, 110, 263

[56] References Cited

U.S. PATENT DOCUMENTS

| | | |
|---|---|---|
| 3,368,558 | 2/1968 | Sarnoff et al. |
| 5,180,370 | 1/1993 | Gillespie . |
| 5,267,972 | 12/1993 | Anderson ................ 604/192 |
| 5,300,030 | 4/1994 | Crossman et al. ........... 604/192 X |
| 5,338,310 | 8/1994 | Lewandowski ............. 604/198 X |
| 5,370,628 | 12/1994 | Allison et al. ............. 604/192 |
| 5,415,648 | 5/1995 | Malay et al. ............. 604/196 X |
| 5,460,611 | 10/1995 | Alexander . |

FOREIGN PATENT DOCUMENTS

| | | |
|---|---|---|
| 405039 | 1/1991 | European Pat. Off. . |
| 467173 | 1/1992 | European Pat. Off. . |
| 497220 | 8/1992 | European Pat. Off. . |
| 1084947 | 1/1955 | France . |
| 2700959 | 8/1994 | France . |
| 2202747 | 10/1988 | United Kingdom . |
| 95 09022 | 4/1995 | WIPO . |

Primary Examiner—Wynn Wood Coggins
Assistant Examiner—A. T. Nguyen
Attorney, Agent, or Firm—Sughrue, Mion, Zinn, Macpeak & Seas, PLLC

[57] ABSTRACT

The injection syringe (10) includes, on the one hand, an elongate syringe body (12) comprising a tube (16) and a front wall (20) equipped with an injection needle (22), and, on the other hand, a rear actuating plunger (14) mounted so as to be displaceable inside the tube (16). The body (12) additionally has a mobile needle protector (36) which can be displaced, under the effect of the actuating plunger (14) driven into the body (12), between a retracted position, set back from the injection end (22A) of the needle (22), and an active protection position, in which the front end of the protector is situated in front of the injection end (22A) of the said needle (22).

10 Claims, 2 Drawing Sheets

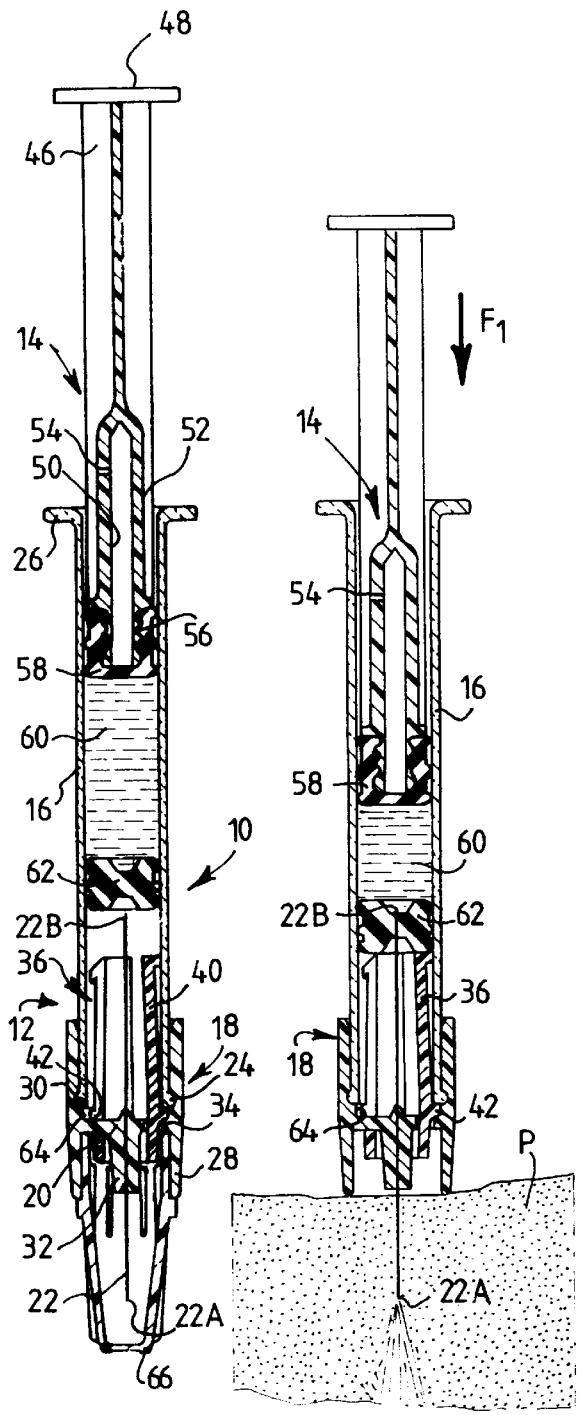
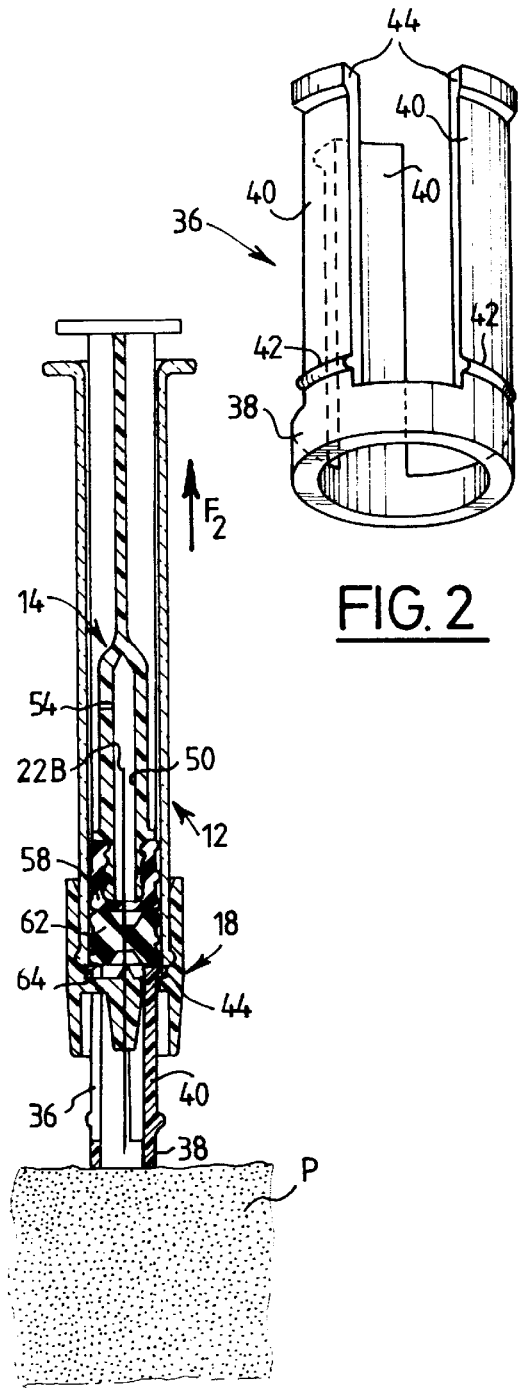
FIG. 1
FIG. 2
FIG. 3
FIG. 4

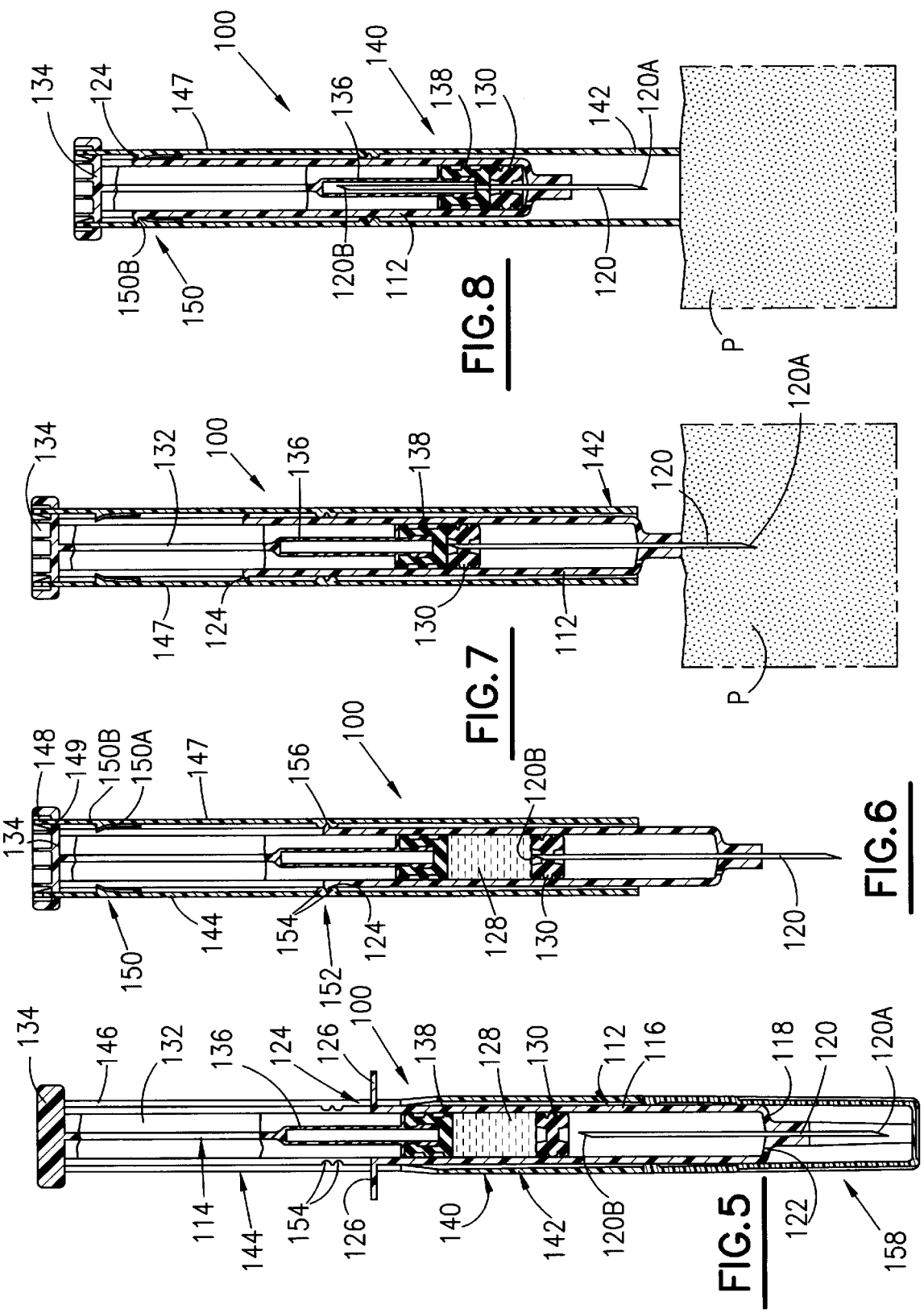

SELF-PROTECTED INJECTION SYRINGE

BACKGROUND OF THE INVENTION

The present invention relates to an injection syringe of the type including, on the one hand, an elongate syringe body comprising a tube and a front wall equipped with an injection needle, and, on the other hand, a rear actuating plunger mounted so as to be displaceable inside the tube.

Syringes of the abovementioned type are known which are used in particular for performing subcutaneous or intramuscular injections in the body of a patient.

The growth of diseases transmitted via the blood has led to the development of disposable syringes which are discarded after the injection has been completed. These syringes can be supplied either filled with the substance to be injected, or else empty, in which case the substance to be injected is pumped through the injection needle by means of the suction obtained on pulling the rear plunger.

The known syringes present a danger to the operator immediately after the withdrawal of the needle from the patient's body at the end of the injection. This is because the operator risks pricking himself or herself with the point of the needle and being contaminated by the residual traces of blood which it bears.

In order to limit the danger presented by the point of the needle, protective caps have been proposed which the operator fits onto the syringe body in order to cover the needle. However, given that the cap has to be put into position manually, the operator may forget to fit it, or else may be pricked by the needle when putting the cap into place. Moreover, the cap cannot be put into place at the same time as the needle is being withdrawn from the patient's body, and so the needle remains unprotected for a brief moment.

SUMMARY OF THE INVENTION

The object of the invention is to make available an injection syringe which eliminates any risk of the operator being pricked by the point of the needle after the end of the injection.

To this end, the invention relates to an injection syringe of the abovementioned type, which is characterized in that it is equipped with a mobile needle protector which can be displaced in relation to the body, under the effect of the actuating plunger being driven into the body, and during this actuation, between a retracted position, set back from the injection end of the needle, and an active protection position, in which the front end of the protector is situated in front of the injection end of the said needle.

Depending on specific embodiments, the invention can have one or more of the following characteristics:

- the body includes at least one opening for the passage of the protector, of which a rear end, situated inside the syringe body, forms a surface for actuation by the rear plunger for the forward displacement of the protector;
- the injection needle protrudes inside the syringe body, and the inside of the tube is provided with a mobile front plunger interposed between the protector and the rear actuating plunger, the two plungers delimiting a space for the fluid which is to be injected;
- prior to the use of the syringe, the front plunger is arranged behind the needle, and the front plunger is designed to be punctured by the proximal end of the needle when the rear plunger is driven in;
- the protector and the body include complementary means for temporarily maintaining the protector in its retracted position, these means being designed to withstand the thrust exerted by the front plunger on the protector when the rear plunger is being driven into the tube, while the rear plunger is behind the proximal end of the needle or the said front plunger;
- the opening, or each opening, is formed in the front wall;
- the protector includes a protective ring arranged outside the body around the axis of the needle, which ring is continued via at least one leg received in an opening of the body, and, in the active protection position, surrounds the injection end of the needle;
- the mobile needle protector is mounted so as to slide on the outside of the syringe body;
- the mobile needle protector includes, on the one hand, an end sheath for protecting the needle, and, on the other hand, means for connecting the said end sheath to the actuating plunger, which connecting means extend externally along the syringe body as far as the end of the plunger protruding from the body;
- the mobile needle protector is fixed to the actuating plunger;
- the mobile needle protector and the syringe body include complementary means for temporarily maintaining the protector in its retracted position;
- the mobile needle protector is essentially tubular and includes longitudinal slots, the syringe body including, at its open end, radial actuating lugs which protrude from the said mobile needle protector through the said slots;
- the protector and the body include complementary means for locking the protector on the body in its active protection position;
- the locking means include complementary protruding and hollowed portions formed on the inner wall of the syringe body and on the leg, or each leg, of the protector;
- the injection needle protrudes inside the syringe body, and the rear plunger is equipped, opposite the proximal end of the needle, with a sealing membrane which can be punctured by the said proximal end of the needle once the plunger has been driven into the body;
- the rear plunger is connected to an actuating rod including an axial recess for receiving the proximal end of the needle, arranged behind the said membrane; and
- the said recess is delimited by a solid wall equipped with one or more calibrated vents for communication with the surrounding atmosphere.

The invention will be better understood on reading the following description which is given solely by way of example and in which reference is made to the drawings, in which:

BRIEF DESCRIPTION OF THE DRAWINGS

FIG. 1 is a longitudinal sectional view of a syringe according to the invention, before use;

FIG. 2 is a perspective view, on an enlarged scale, of the protector for the needle of the syringe in FIG. 1;

FIG. 3 is a longitudinal sectional view of the syringe in FIG. 1, represented during the injection of the fluid into a patient's body;

FIG. 4 is a longitudinal sectional view of the same syringe immediately after the withdrawal of the needle from the patient's body;

FIG. 5 is a longitudinal sectional view of an alternative embodiment of a syringe according to the invention, before use;

FIG. 6 is a longitudinal sectional view of the syringe in FIG. 5 offset angularly by 90°, immediately before the injection of the fluid into a patient's body;

FIG. 7 is a longitudinal sectional view of the same syringe at the end of the injection; and FIG. 8 is a longitudinal sectional view of the same syringe after the withdrawal of the needle from the patient's body.

DESCRIPTION OF PREFERRED EMBODIMENTS

The injection syringe 10 represented in FIG. 1, of a general shape with axis of revolution X—X, is a disposable syringe offered ready for use and already containing a medical fluid to be injected. It includes essentially an elongate syringe body 12 and a rear actuating plunger 14 which is mounted so as to be displaceable inside the body 12.

The syringe body 12 is formed by a tube 16, at the front end of which there is fixed a needle holder 18 bearing a front wall 20 of the syringe body. This front wall 20 is equipped with an injection needle 22 passing through it, of which a rear end 22B protrudes inside the body 12.

The tube 16 is made of glass, for example, and has a circular cross-section. Its front end is equipped externally with a peripheral bead 24 for supporting the needle holder 18. Its rear end has an external peripheral shoulder 26 making it easier to grip the syringe body between the index finger and middle finger.

The needle holder 18 is delimited externally by a sleeve 28. The front wall 20 is formed integral with the sleeve 28 and extends transversely from an intermediate point on the latter. Provided on the inner wall of the sleeve 28, slightly to the rear of the front wall 20, there is a peripheral groove 30 for receiving the bead 24.

The front wall 20 has an axial stud 32, formed integral with it, for securing the injection needle 22. This stud is directed toward the injection end 22A of the needle 22 and is received inside the space delimited by the sleeve 28.

Three identical openings 34 are formed through the front wall 20. They are distributed at uniform angles about the stud 32 on one circular contour, and they have an arched shape.

These openings 34 provide for the passage and the guidance of a needle protector 36 which is represented in greater detail in FIG. 2. It has, at the front, a protective ring 38 made of a rigid plastic, and the internal and external diameters of this ring 38 are adapted so that it can lodge itself in the annular space defined between the stud 32 and the sleeve 28. This ring is continued via three identical legs 40 which are elastically deformable and spaced at angles of 120°. These legs 40 present, in section, a slight curvature corresponding to that of the ring 38, and they have a length which is slightly less than the length of the part of the needle 22 received in the syringe body 12.

Furthermore, each leg 40 includes externally, over its entire width, a first bulge 42 which is arranged slightly to the rear of the ring 38, and a second bulge 44 which is arranged at its free end.

The rear plunger 14 includes an elongate pusher 46, with a cross-shaped section, and has at its rear end a block 48 to support the operator's thumb. Provided axially at its opposite end there is a recess 50 which opens to the front and which serves to receive the rear or proximal end 22B of the needle 22 at the end of the injection. This recess 50, of elongate shape along the axis X—X, has a circular cross-section. It is delimited by a cylindrical wall 52 which is equipped with a calibrated vent 54.

The wall 52 has on its outside, at its front end, three successive annular beads 56 for secure engagement of a trough-shaped end membrane 58. This membrane closes off the main front opening of the recess 50 and is designed so as to slide in a leaktight manner inside the tube 16.

As is represented in FIG. 1, the fluid to be injected 60 is arranged inside the tube 16 in a space delimited by a front plunger 62 and the membrane 58 of the rear plunger 14. The front plunger 62 is formed by a transverse partition which can be punctured and which is surrounded by a cylindrical lateral wall which is equipped with peripheral ribs in order to guarantee the liquid tightness and gas tightness between itself and the inner lateral wall of the tube 16.

The front end of the tube 16 is fitted in the sleeve 28 and is fixed there by adhesive bonding, for example. Since the peripheral groove 30 is set slightly back from the transverse wall 20, the latter delimits, together with the front end of the tube 16, an annular channel 64 which is arranged immediately to the rear of the wall 20, and the bottom of which is formed by the sleeve 28.

The plunger 62 is positioned slightly to the rear of the proximal end 22B of the injection needle.

The protector 36 is mounted through the front wall 20 in such a way that the front protective ring 38 surrounds the stud 32 and that the legs 40, engaged in the respective openings 34, extend inside the syringe body 12. In the position represented in FIG. 1, corresponding to the retracted position of the protector 36, the bulges 42 are received inside the channel 64, thus temporarily maintaining the protector in its retracted position.

Furthermore, a protective cap 66 for the needle 22 is fitted inside the sleeve 28 and covers the injection end 22A of the needle.

To proceed with the injection, the operator removes the cap 66, then introduces the injection end 22A of the needle into the tissues of a patient P, as is represented in FIG. 3. Here, in the usual way, the operator uses his thumb to push the rear plunger 14 in the direction of the arrow F1, while resting his index finger and middle finger under the shoulder 26.

The pressure thus exerted, and transmitted by way of the liquid 60 to the front plunger 62, causes the latter to be displaced toward the proximal end 22B of the needle, and to be punctured. The displacement of the front plunger 62 impaled on the needle is stopped when the plunger comes into contact with the rear ends of the legs 40 of the protector, as is represented in FIG. 3.

For this purpose, the bulges 42 and the channel 64, forming locking means, are dimensioned in such a way that the protector 36 is maintained in its retracted position despite the pressure exerted by the front plunger. The fluid 60 then flows through the needle 22 under the effect of the pushing of the rear plunger 14. When the bulk of the fluid 60 has been injected, the membrane 58 comes into contact with the rear surface of the front plunger 62. The continued pressure exerted by the operator on the rear plunger causes the bulges 42 to disengage from the channel 64 by means of elastic deformation of the legs 40. This is followed by the forward displacement of the protector 36. When the ring 38 comes into contact with the patient's skin, the travel of the protector is stopped, and the continued closing together of the thumb, pressing on the block 48, and of the index finger and middle finger, held against the shoulder 26, causes the syringe body 12 to ascend in the direction of arrow F2.

It will be appreciated that, as represented in FIG. 4, the upward movement of the body 12 causes the withdrawal of the injection needle 22 from the patient's body P. Furthermore, the rear end 22B of the needle pierces the membrane 58 and is received in the recess 50.

The upward movement of the syringe body 12 continues until the end bulges 44 lock in the annular channel 64. The protector 36 is then in the active protection position and extends around the needle 22. The front face of the protective ring 38 is then situated slightly in front of the end 22A of the injection needle, and the ring 38 surrounds this end, prohibiting any contact between this end and an external element, and thus preventing any risk to the operator of contamination by pricking. Furthermore, the bulges 44 received in the channel 64 maintain the protector 36 firmly in the protection position, thereby prohibiting any accidental retraction.

Since the membrane 58 has been punctured by the rear end 22B of the needle, any subsequent reuse of the syringe is rendered impossible. This is because this puncture prohibits the suction effect which is normally obtained inside the body upon the backward movement of the rear plunger, on account of the presence of the vent 54. Likewise, the punctured rear plunger does not permit expulsion, by the injection needle 22, of any liquid reintroduced into the syringe body.

For this purpose, the vent 54 is dimensioned in such a way that air can circulate through it when there is a difference in pressure between the recess 50 and the surrounding atmosphere, due, for example, to the displacement of the rear plunger, but in such a way that no passage of liquid takes place in the event of a slight pressure difference. Thus, at the end of the injection, when the end 22A of the needle is still introduced in the patient's tissues, a possible reflux of blood through the needle 22, under the effect of the blood pressure, does not allow the blood to leave the recess 50 via the vent 54.

The syringe described here is a syringe which is filled at the time of its production and which is offered ready for use. However, the use of a protector, and of a rear plunger equipped with a membrane which can be punctured, is also possible in the case of a syringe which is offered empty and which is intended to be filled before proceeding with the injection. In this case, the syringe is offered with the front plunger 62 punctured, engaged on the needle 22, and in contact against the rear end of the legs 40 of the protector. Furthermore, the rear plunger 14 is arranged in such a way that the membrane 58 is immediately behind the proximal end 22B of the needle.

Under these conditions it is possible, by pulling on the rear plunger 14, to draw the injection liquid by suction through the needle 22. The injection of the liquid into the patient's body follows the same steps as those described above, with the exception of the first step consisting in puncturing the front plunger 62.

Alternatively, for such a syringe offered for sale empty, the front plunger 62 can be omitted. The leaktightness at the point where the legs 40 pass through the openings 34 is in this case ensured by means of a precise fit or by means of a flexible membrane covering the protector.

FIGS. 5 to 8 represent an alternative embodiment of an injection syringe according to the invention.

The injection syringe represented, bearing the general reference 100, is, as before, a disposable syringe offered ready for use and already containing a medical fluid to be injected. It includes essentially a syringe body 112 and an actuating plunger 114 which is mounted so as to be displaceable inside the body 112.

The syringe body 112, which is made of a plastic material for example, consists of a tube 116 which is closed off at one end by an integrally formed front wall 118. The front wall is traversed axially by an injection needle 120, of which one front end 120A protrudes outside the body. The other end 120B protrudes inside the body. A vent 122 passes through the front wall 118.

The rear end of the tube 116 is open and is bordered laterally by a peripheral shoulder 124 including two diametrically opposite, radial lugs 126 which form support surfaces for the operator's fingers during actuation of the syringe.

The syringe body 112 contains a fluid to be injected 128, maintained between a front plunger 130, which can be punctured, and the rear actuating plunger 114.

The latter includes, as in the preceding embodiment, a pusher 132 whose structure is substantially analogous to the pusher 46. Thus, it includes an actuating block 134 at its rear end and, at its front end, a recess 136 equipped with a calibrated vent. The recess 136, open to the front, is closed off by a membrane 138.

The pusher 132 is integral with a mobile needle protector 140 which is mounted such that it can be displaced along the outside of the body 112. The needle protector 140 has an essentially tubular form. At its front end it includes a cylindrical portion 142 forming a sheath. The latter is continued rearwards by means 144 for connection to the pusher 132. These connection means include a tubular portion (FIG. 6) which is formed integrally with the front portion 142 and which is cut longitudinally with two opposite slits 146 which are open to the front and via which the tongues 126 protrude. The slits 146 thus delimit between each other, on the tubular portion 144, two connecting legs 147 of curved cross-section.

At their free end, the two connecting legs 147 include locking means 148 passing through slots 149 in the block 134. After locking, the rear end of the protector 140 is adhesively bonded or welded by ultrasound to the block 134.

The connecting legs 147 include on the inside, in front of the block 134, locking means 150 designed to cooperate with the external peripheral shoulder 124 formed at the end of the syringe body. These locking means 150 include, for example, a ramp 150A whose height gradually increases from the front rearward, followed by an edge face 150B.

In addition, the connecting legs 147 include, in front of the locking means 150, means 152 for temporarily maintaining the needle protector in a retracted position on the syringe body. These means 152 include, for example, two annular bosses 154 formed internally on the connecting legs 147 and delimiting between each other a groove 156 for receiving the peripheral shoulder 124, as is represented in FIG. 6.

A removable protective cap 158 is arranged at the front end of the syringe in order to cover the end 120A of the needle.

To assemble such a syringe, the syringe body 112 is first produced, in which body the needle 120 is incorporated. The front plunger 130, the liquid 128 and the rear plunger 114, equipped beforehand with the membrane 138, are then arranged in the syringe body. The syringe body 112 is then introduced via the rear into the needle protector 140, the radial lugs 126 being arranged in the slits 146. During this assembling, the shoulder 124 is engaged beyond the locking means 150, with which it normally cooperates. This is made possible by the elastic deformation of the legs 147, the rear end of which is free. The rear ends of the connecting legs 147 are then locked in the slots 149 of the block 134, where they are finally adhesively bonded or welded by ultrasound in order to ensure the secure attachment of the plunger 114 and the needle protector 140. The cap 158 is finally put in place so as to cover the needle.

In the position represented in FIG. 5, corresponding to the state in which the syringe is supplied, the front plunger 130 is spaced rearward from the end 120B of the needle. Thus, the fluid 128 is not in contact with the needle. The needle protector 140 is in this case retracted on the body of the syringe, the protective sheath 142 covering the tube 116.

In order to use the syringe, after the cap 158 has been removed, the plunger 114 is driven slightly into the syringe body, in such a way that the front plunger 130 is impaled on the end 120B of the needle, as is represented in FIG. 6. Before the fluid 128 flows through the needle 120, the shoulder 124 snaps into the groove 156, thereby ensuring, prior to the injection, that the needle protector is temporarily maintained on the syringe body. The needle end 120A is then exposed, the protective sheath 142 being arranged entirely to the rear on the body 112.

After introducing the end 120A of the needle into the patient's body, as is represented in FIG. 7, the plunger 114 is driven progressively into the syringe body 112, which causes the fluid 128 to be injected, by means of the plunger 114 moving toward the front plunger 130. As the plunger is driven in, the needle protector 140 is displaced axially forward along the syringe body as far as the position represented in FIG. 7, where all the fluid 128 has been injected.

After complete injection of the fluid 128, the continued driving of the plunger through the syringe body causes the front end of the needle protector 140 to come into contact with the surface of the patient's skin. Once the end of the protector is resting on the skin, the continued sliding of the body in relation to the needle protector causes the syringe body 112 to ascend inside the protector 140. During this phase, the plunger 130 is displaced toward the front wall 118, and the air contained in the chamber delimited between the plunger 130 and this wall 118 escapes through the vent 122.

As is represented in FIG. 8, at the end of the ascending movement of the syringe body, the needle protector 140 is in the active protection position. In this position, the protective sheath 142 is situated to the front of the injection end 120A of the needle. It completely surrounds the latter, thereby preventing any risk of accidental pricking.

In addition, the shoulder 124 is snapped behind the edge face 150B of the locking means 150, guaranteeing the definitive retention of the syringe body 112 and of the needle 120 inside the needle protector 140.

What is claimed is:

1. In an injection syringe (10; 100) of the type including, on the one hand, an elongate syringe body (12; 112) comprising a tube (16; 116) and a front wall (20; 118) equipped with an injection needle (22; 120), and, on the other hand, a rear actuating plunger (14; 114) mounted so as to be displaceable inside the tube (16; 116), the improvement wherein:

said syringe is equipped with a mobile needle protector (36, 140) which is displaceable in relation to the body (12; 112), under the effect of the actuating plunger (14; 114) being actuated and driven into the body (12; 112), and during this actuation, between a retracted position, set back from the injection end (22A; 120A) of the needle (22; 120), and an active protection position, in which the front end of the protector is situated in front of the injection end (22A; 120A) of the needle (22; 120);

the body (12) includes at least one opening (34) for the passage of the protector (36), of which a rear end (44), situated inside the syringe body (12), forms a surface for actuation by the rear plunger (14) for forward displacement of the protector (36);

the injection needle (22) protrudes inside the syringe body (12), and the inside of the tube (16) is provided with a mobile front plunger (62) interposed between the protector (36) and the rear actuating plunger (14), the two plungers delimiting a space for fluid (60) which is to be injected;

prior to use of the syringe, the front plunger (62) is arranged behind the needle (22), and the front plunger (62) is designed to be punctured by the proximal end (22B) of the needle (22) when the rear plunger (14) is driven in; and the protector (36) and the body (12) include complementary means (42, 64) for temporarily maintaining the protector (36) in its retracted position, said means being designed to withstand thrust exerted by the front plunger (62) on the protector (36) when the rear plunger (14) is being driven into the tube (16), while the rear plunger (14) is behind the proximal end (22B) of the needle (22) or the front plunger (62).

2. The injection syringe (10) according to claim 1, wherein the opening (34) is formed in the front wall (20).

3. The injection syringe (10) according to claim 1, wherein the protector (36) includes a protective ring (38) arranged outside the body (12) around the axis (X—X) of the needle (22), which ring (38) is continued via at least one leg (40) received in the opening (34) of the body (12), and, in the active protection position, surrounds the injection end of the needle.

4. The injection syringe (10) according to claim 3, wherein:

the protector (36; 140) and the body (12; 112) include complementary means (44; 64; 150) for locking the protector (36; 140) on the body (12; 112) in its active protection position; and the complementary means (44, 64) include complementary protruding (44) and hollowed (64) portions formed on the inner wall of the syringe body (12) and on the leg (40) of the protector (36).

5. In an injection syringe (10; 100) of the type including, on the one hand, an elongate syringe body (12; 112) comprising a tube (16; 116) and a front wall (20; 118) equipped with an injection needle (22; 120), and, on the other hand, a rear actuating plunger (14; 114) mounted so as to be displaceable inside the tube (16; 116), the improvement wherein:

said syringe is equipped with a mobile needle protector (36, 140) which is attached to the actuating plunger, and which is displaceable in relation to the body (12; 112), under the effect of the actuating plunger (14; 114) being actuated and driven into the body (12; 112), and during this actuation, between a retracted position, set back from the injection end (22A; 120A) of the needle (22; 120), and an active protection position, in which the front end of the protector is situated in front of the injection end (22A; 120A) of the needle (22; 120);

the mobile needle protector (140) is mounted so as to slide on the outside of the syringe body (112).

6. The injection syringe (100) according to claim 5, wherein the mobile needle protector (140) includes, on the one hand, an end sheath (142) for protecting the needle (120), and, on the other hand, means (144) for connecting the end sheath (142) to the actuating plunger (114), said connecting means (144) extending externally along the syringe body (112) as far as the end of the plunger (114) protruding from the body (112).

7. The injection syringe (100) according to claim 6, wherein the mobile needle protector (140) is fixed to the actuating plunger (114).

8. The injection syringe (100) according to claim 5, wherein the mobile needle protector (140) and the syringe body (112) include complementary means (152) for temporarily maintaining the protector (140) in its retracted position.

9. The injection syringe (100) according to claim 5, wherein the mobile needle protector (140) is essentially tubular and includes longitudinal slits (146), the syringe body (112) including, at its open end, radial actuating lugs (126) which protrude from the mobile needle protector (140) through said slits (146).

10. In an injection syringe (10; 100) of the type including, on the one hand, an elongate syringe body (12; 112) comprising a tube (16; 116) and a front wall (20; 118) equipped with an injection needle (22; 120), and, on the other hand, a rear actuating plunger (14; 114) mounted so as to be displaceable inside the tube (16; 116), the improvement wherein:

said syringe is equipped with a mobile needle protector (36, 140) which is displaceable in relation to the body (12; 112), under the effect of the actuating plunger (14; 114) being actuated and driven into the body (12; 112), and during this actuation, between a retracted position, set back from the injection end (22A; 120A) of the needle (22; 120), and an active protection position, in which the front end of the protector is situated in front of the injection end (22A; 120A) of the needle (22; 120);

the injection needle (22; 120) protrudes inside the syringe body (12; 112), and the rear plunger (14, 114) is equipped, opposite the proximal end (22B; 120B) of the needle (22; 120), with a sealing membrane (58; 138) which is punctured by the proximal end (22B; 120B) of the needle (22; 120) once the plunger (14; 114) has been driven into the body (12; 112);

the rear plunger (14; 114) is connected to an actuating rod (46; 132) including an axial recess (50; 136) for receiving the proximal end (22B; 120B) of the needle (22; 120), arranged behind the said membrane (58; 138); and said recess (50; 136) is delimited by a solid wall (52) equipped with one or more calibrated vents (54) for communication with the surrounding atmosphere.

* * * * *